US010373838B2

(12) United States Patent
Uhlmeyer et al.

(10) Patent No.: US 10,373,838 B2
(45) Date of Patent: Aug. 6, 2019

(54) AUTOMATIC SAMPLING OF HOT PHOSPHORIC ACID FOR THE DETERMINATION OF CHEMICAL ELEMENT CONCENTRATIONS AND CONTROL OF SEMICONDUCTOR PROCESSES

(71) Applicant: Elemental Scientific, Inc., Omaha, NE (US)

(72) Inventors: Kyle W. Uhlmeyer, Omaha, NE (US); Jae Seok Lee, Omaha, NE (US); Daniel R. Wiederin, Omaha, NE (US); Patrick Sullivan, Omaha, NE (US)

(73) Assignee: ELEMENTAL SCIENTIFIC, INC., Omaha, NE (US)

( * ) Notice: Subject to any disclaimer, the term of this patent is extended or adjusted under 35 U.S.C. 154(b) by 210 days.

(21) Appl. No.: 15/366,250

(22) Filed: Dec. 1, 2016

(65) Prior Publication Data

US 2017/0162457 A1 Jun. 8, 2017

Related U.S. Application Data

(60) Provisional application No. 62/264,740, filed on Dec. 8, 2015.

(51) Int. Cl.
*G01N 1/10* (2006.01)
*H01L 21/306* (2006.01)
(Continued)

(52) U.S. Cl.
CPC ..... *H01L 21/30604* (2013.01); *G01N 1/2035* (2013.01); *G01N 35/1097* (2013.01);
(Continued)

(58) Field of Classification Search
CPC ........... G01N 1/28; G01N 1/00; G01N 1/286; G01N 1/38; G01N 1/10; H01L 2924/0002;
(Continued)

(56) References Cited

U.S. PATENT DOCUMENTS 3,314,756 A * 4/1967 Rene Myon ............. B01D 1/06
159/47.1
3,623,913 A * 11/1971 Adlhart et al. ..... H01M 8/0606
429/434
(Continued)

OTHER PUBLICATIONS

Office Action dated Mar. 13, 2018 for Taiwan Patent Appln. No. 105140568.

*Primary Examiner* — Peter J Macchiarolo
*Assistant Examiner* — Mohammed E Keramet-Amircolai
(74) *Attorney, Agent, or Firm* — Kevin E. West; Advent, LLP

(57) ABSTRACT

Systems and methods for automatic sampling of a sample for the determination of chemical element concentrations and control of semiconductor processes are described. A system embodiment includes a remote sampling system configured to collect a sample of phosphoric acid at a first location, the remote sampling system including a remote valve having a holding loop coupled thereto; and an analysis system configured for positioning at a second location remote from the first location, the analysis system coupled to the remote valve via a transfer line, the analysis system including an analysis device configured to determine a concentration of one or more components of the sample of phosphoric acid and including a sample pump at the second location configured to introduce the sample from the holding loop into the transfer line for analysis by the analysis device.

20 Claims, 5 Drawing Sheets

(51) Int. Cl.
  *G01N 35/10*   (2006.01)
  *G01N 1/20*    (2006.01)
  *H01L 21/311*  (2006.01)

(52) U.S. Cl.
  CPC ............... *G01N 2001/1062* (2013.01); *G01N 2001/2057* (2013.01); *H01L 21/31111* (2013.01)

(58) Field of Classification Search
  CPC ............ H01L 22/20; H01L 21/30604; H01L 21/67075; H01L 21/67253; H01L 21/66; H01L 21/67; H01L 21/306
  USPC ......................................................... 73/863
  See application file for complete search history.

(56) References Cited

U.S. PATENT DOCUMENTS

| | | | |
|---|---|---|---|
| 2001/0023130 A1* | 9/2001 | Gilton | G01N 1/32 438/689 |
| 2010/0032587 A1  | 2/2010 | Hosch et al. | |
| 2010/0089142 A1* | 4/2010 | Sukhija | C09K 8/58 73/152.39 |
| 2010/0183869 A1* | 7/2010 | Lin | B22D 17/00 428/332 |
| 2013/0034497 A1* | 2/2013 | Schmitt-Willich | C07B 59/001 424/1.85 |
| 2016/0145164 A1* | 5/2016 | Palmer | C05G 3/0094 504/101 |

* cited by examiner

AUTOMATIC SAMPLING OF HOT PHOSPHORIC ACID FOR THE DETERMINATION OF CHEMICAL ELEMENT CONCENTRATIONS AND CONTROL OF SEMICONDUCTOR PROCESSES

CROSS-REFERENCE TO RELATED APPLICATIONS

The present application claims the benefit under 35 U.S.C. § 119(e) of U.S. Provisional Application Ser. No. 62/264,740, filed Dec. 8, 2015, and titled "AUTOMATIC SAMPLING OF HOT PHOSPHORIC ACID FOR THE DETERMINATION OF CHEMICAL ELEMENT CONCENTRATIONS AND CONTROL OF SEMICONDUCTOR PROCESSES." U.S. Provisional Application Ser. No. 62/264,740 is herein incorporated by reference in its entirety.

BACKGROUND

Spectrometry refers to the measurement of radiation intensity as a function of wavelength to identify component parts of materials. Inductively Coupled Plasma (ICP) spectrometry is an analysis technique commonly used for the determination of trace element concentrations and isotope ratios in liquid samples. For example, in the semiconductor industry, ICP spectrometry can be used to determine metal concentrations in samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample. The sample to be analyzed is often provided in a sample mixture.

Sample introduction systems may be employed to introduce liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods for automatic sampling of a sample for the determination of chemical element concentrations and control of semiconductor processes are described. A system embodiment includes a remote sampling system configured to collect a sample of phosphoric acid at a first location, the remote sampling system including a remote valve having a holding loop coupled thereto; and an analysis system configured for positioning at a second location remote from the first location, the analysis system coupled to the remote valve via a transfer line, the analysis system including an analysis device configured to determine a concentration of one or more components of the sample of phosphoric acid and including a sample pump at the second location configured to introduce the sample from the holding loop into the transfer line for analysis by the analysis device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. In the figures, the use of the same reference numbers in different instances in the description and the figures may indicate similar or identical items.

DETAILED DESCRIPTION

Figure 1:
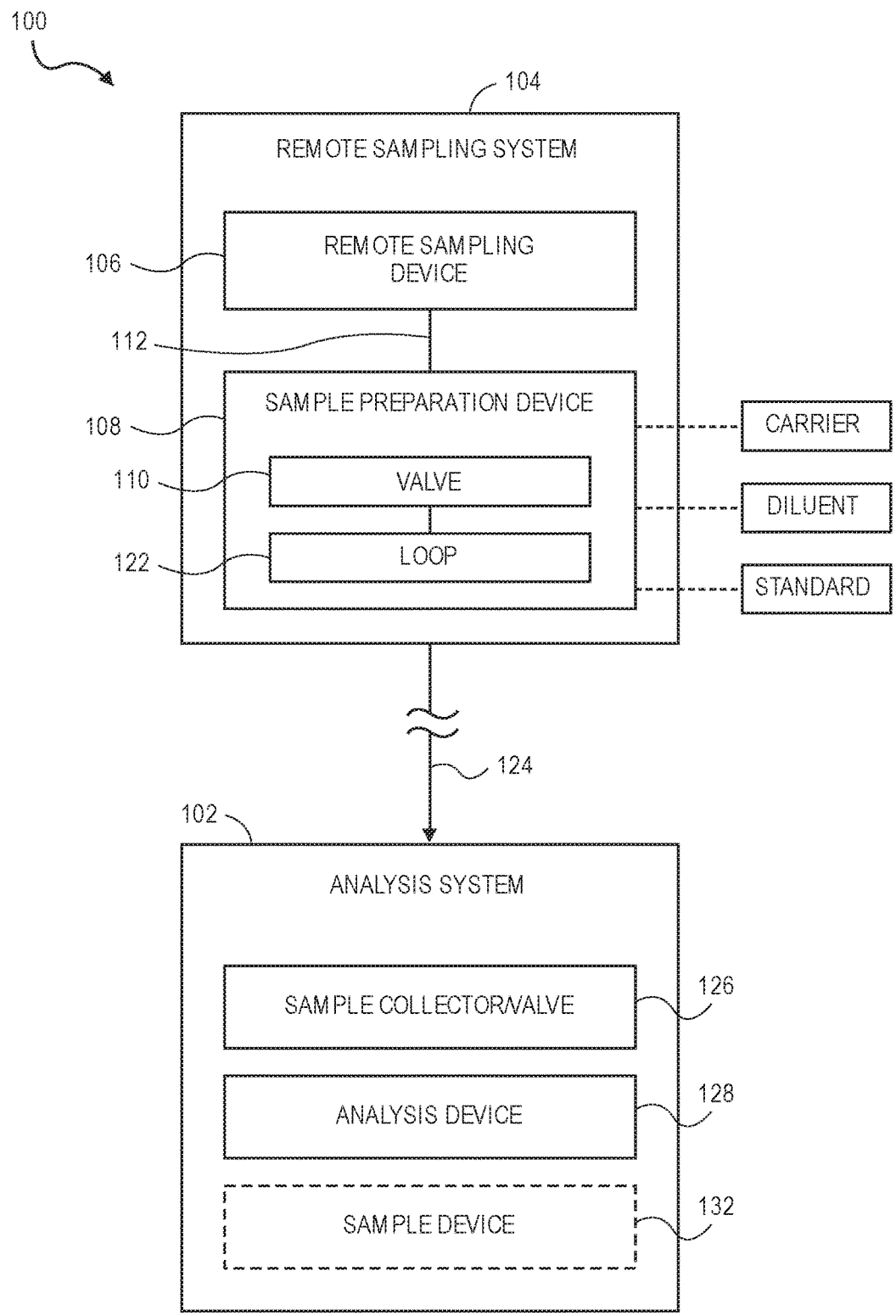
FIG. 1 is a schematic illustration of a remote analysis system for automatic analysis of chemical element concentrations in accordance with example implementations of the present disclosure.

Referring to FIGS. 1-5, systems and methods for automatic sampling of a sample (e.g., hot phosphoric acid) for the determination of chemical element concentrations and control of semiconductor processes are described. For semiconductor fabrication, certain etching techniques can be utilized to chemically remove layers of a semiconducting wafer with precise control. For example, with nitride semiconducting wafers, the nitride film can be precisely etched without damaging the other components or layers. Such etching can be facilitated by a wet etching process using hot phosphoric acid (e.g., phosphoric acid ($H_3PO_4$) having a temperature from about 150° C. to about 180° C.), where the etch rate is dependent upon the concentration of silicon in the hot phosphoric acid. Control of the timing of the etching processes can therefore depend on precise control of the amount of silicon in the phosphoric acid. Too much silicon in the phosphoric acid can substantially slow or essentially stop the etch rate, whereas too little silicon in the phosphoric acid can cause the etch rate to be too fast, potentially damaging the device being fabricated. Further, the concentration of silicon in the hot phosphoric acid can change over time, since the etching process itself adds silicon to the phosphoric acid bath, thereby altering the silicon concentration.

Accordingly, the present disclosure is directed to systems and methods for automatic sampling of hot phosphoric acid for the determination of chemical element concentrations and control of semiconductor processes. In implementations, the systems and methods include sampling and analyzing hot phosphoric acid for accurate determination of concentrations of metals (e.g., silicon, tungsten, copper, titanium, etc.) and non-metals using one or more of remote dilution of the hot phosphoric acid sample or heated transfer of the hot phosphoric acid sample. The sample can be transferred from a remote sampling site at a first location to a centralized analyzer system having an ICP or ICP-MS detector at a second location for the determination of chemical element concentrations. In implementations, the system includes a pump system to dilute samples (e.g., hot phosphoric acid samples) at the first location prior to transfer and analysis by the analyzer system. The dilution can include dilutions from about five-fold dilution to about twenty-fold dilution. In implementations, the dilution factor can be lower (e.g., lower than five-fold dilution) or higher (e.g., up to about one-hundred-fold dilution). Further, the systems and methods can include determination of the chemical element concentrations, reporting of the chemical element concentration data (e.g., via one or more communications protocols), and automatic control of semiconductor processing conditions based upon the chemical element concentration data (e.g., feedback responsive control of hot phosphoric acid relative to nitride etching).

In the following discussion, example implementations of techniques for automatic sampling of hot phosphoric acid for the determination of chemical element concentrations and control of semiconductor processes are presented.

Example Implementations

Referring generally to FIGS. 1 through 5, example systems configured to analyze samples transported from a remote sampling site at a first location over one or more distances to a centralized analyzer system at a second location are described. In implementations, the samples include hot phosphoric acid used for semiconductor manufacturing processes, including chemical etching processes for silicon (e.g., nitride wet etching). During such processing, the hot phosphoric acid at a sample point of the remote sampling site can exceed 150° C., for example, the hot phosphoric acid can be maintained from about 150° C. to about 180° C. Temperatures higher than about 165° C. can result in faster etching or removal of silicon nitride (e.g., $Si_3N_4$), but lower selectivity to silicon oxides (e.g., $SiO_2$) and silicon. A system 100 includes an analysis system 102 at a first location. The system 100 also includes one or more remote sampling systems 104 at a second location remote from the first location. The system 100 can also include one or more remote sampling system(s) 104 at a third location, a fourth location, and so forth, where the third location and/or the fourth location are remote from the first location. In some embodiments, the system 100 also may include one or more sampling system(s) at the first location (e.g., proximate to the analysis system 102). For example, a sampling system at the first location may include a sampling device 132 coupled with the analysis system 102. The one or more remote sampling systems 104 can be operable to receive samples from the second location, the third location, the fourth location, and so forth, and the system 100 can be operable to deliver the samples from the one or more remote sampling systems 104 to the analysis system 102 for analysis. For example, the one or more remote sampling systems 104 can include an autosampler or other sampling device configured to draw a sample from a sampling site into the system 100, such as through aspiration, pump operation (e.g., syringe pump, peristaltic pump, etc.), or the like.

A remote sampling system 104 can be configured to receive a sample 112 from a sampling site and prepare the sample 112 for delivery and/or analysis. In embodiments, the remote sampling system 104 can be disposed various distances from the analysis system 102 (e.g., 1 m, 5 m, 10 m, 50 m, 100 m, 1000 m, etc. between the first location and the second location). In implementations, the remote sampling system 104 can include a remote sampling device 106 and a sample preparation device 108. The sample preparation device 108 may further include a valve 110, such as a multi-port flow-through valve, to facilitate introduction of one or more of carrier fluids, diluents, standards, or other fluids to the remote sampling system 104. In implementations, the remote sampling device 106 can include a device configured for collecting a sample 112 from a sample stream (e.g., a liquid, such as hot phosphoric acid, etc.), such as a sample probe in fluid communication with a vacuum source, pump, or the like. The remote sampling device 106 can include components, such as pumps, valves, tubing, sensors, etc., to facilitate sampling collecting operations, such as timing of sample collection, volume of sample collection, or the like.

Figure 2:
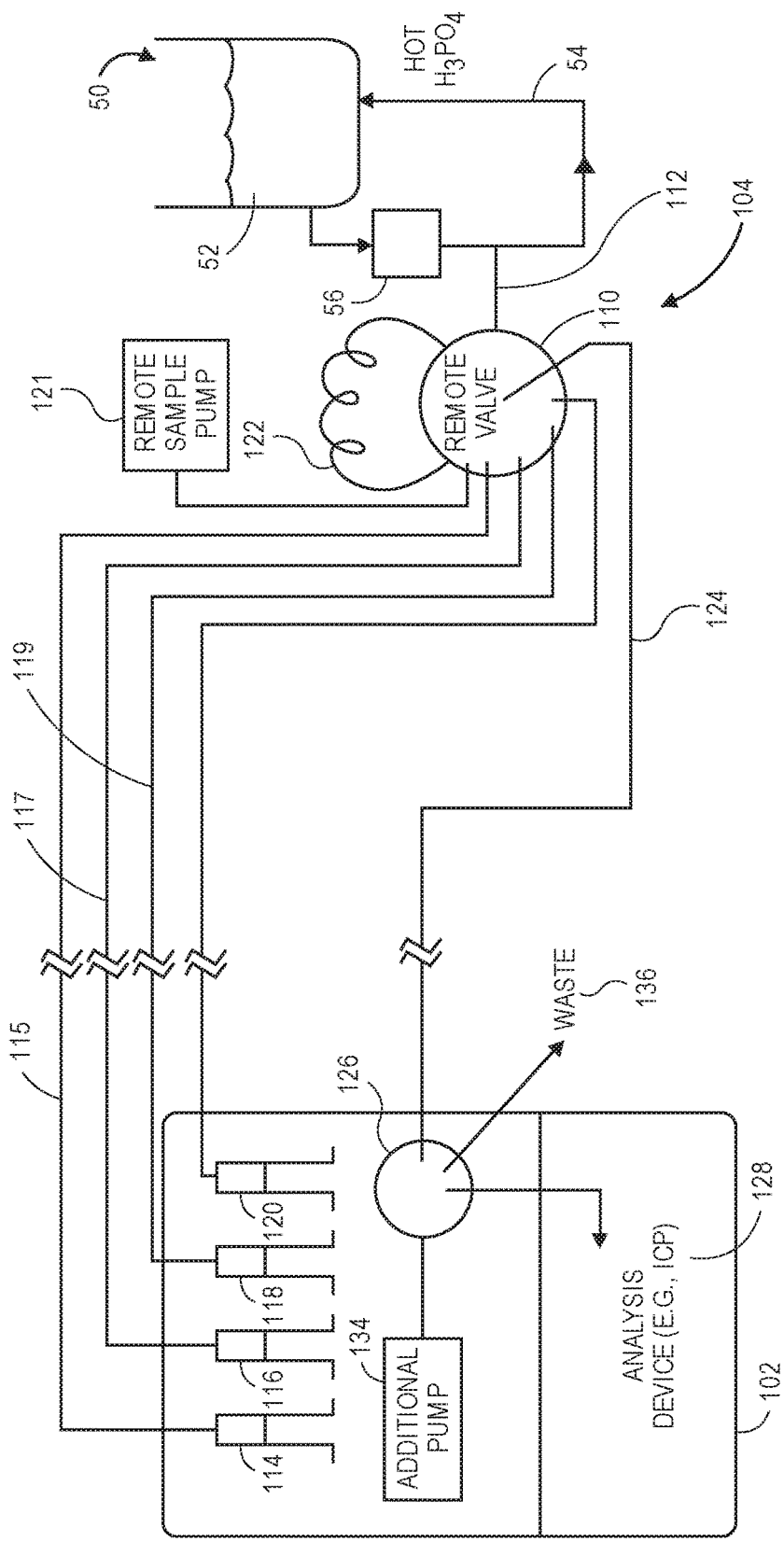
FIG. 2 is a schematic illustration of a system for automatic sampling of hot phosphoric acid and analysis of chemical element concentrations in the phosphoric acid via remote dilution of the sample in accordance with example implementations of the present disclosure.

The sample preparation device 108 can include a device configured to prepare a sample 112 collected from the remote sampling device 106 for analysis via introduction with one or more of a diluent, an internal standard, a carrier, or other fluid, solution, mixture, or the like. In implementations, the diluent, carrier, standard, or other fluid, solution, or mixture can be provided via one or more pumps associated with the first location (e.g., from the analysis system 102) remote from the sampling site. As such, the diluent, carrier, standard, or other fluid, solution, or mixture can remain separated from the second location, third location, fourth location, etc. until a sample is drawn at the respective sampling location at which time the pumps associated with the first location can deliver the appropriate fluids to the respective sampling location for preparation of the sample for transit from the respective sampling location to the first location. For instance, as shown in FIG. 2, the sample 112 can be collected from a semiconductor fabrication process, such as from a hot phosphoric acid etching system 50. The sample 112 can be collected from an acid bath 52 of the etching system 50, from a portion of a recirculation line 54 (e.g., downstream of a filter 56 of the recirculation line 54), or from a combination of sources from the etching system 50, where the hot phosphoric acid is maintained at a temperature from about 150° C. to about 180° C. (e.g., to maintain a relatively low viscosity to facilitate etching, transport, filtering, and the like). In an implementation, the hot phosphoric acid is a concentrated phosphoric acid (e.g., about 85% $H_3PO_4$). The sample 112 is transferred from the remote sampling system 104 to the analysis system 102 via one or more of remote dilution of the hot phosphoric acid sample at the sampling site (e.g., second location) or thermally-controlled transfer of the hot phosphoric acid sample between the sampling site and the first location to permit flow of the phosphoric acid. In implementations, the remote dilution and/or the thermally-controlled transfer facilitates transfer of the phosphoric acid sample through the relatively small fluid flow passageways of the tubing, valves, etc. of the system 100. For example, in an implementation, the system 100 includes tubes, valve ports, or the like having internal diameters from about 0.15 mm to about 2.0 mm.

Remote Dilution

Referring to FIG. 2, the system 100 is shown in an implementation with remote dilution of the sample 112 prior to transferring the sample 112 from the second location (e.g., proximate the etching system 50) to the first location (e.g., proximate the analysis system 102). The analysis system 102 includes a plurality of pumps (e.g., syringe pumps 114, 116, 118, 120) which deliver carrier, diluent, and optionally one or more standard spikes to the valve 110 of the sample preparation device 108 of the remote sampling system 104. For example, as shown, the analysis system 102 includes a carrier pump 114 configured to supply carrier to the valve 110 (e.g., via carrier line 115), a diluent pump 116 configured to supply diluent to the valve 110 (e.g., via diluent line 117), a standard pump 118 configured to supply a standard spike to the valve 110 (as desired, via standard line 119), and a sample pump 120 configured to draw sample 112 from the etching system 50 into the remote sampling system 104. Alternatively, the system 100 can take the sample 112 from the etching system 50 via one or more of a pressure supplied by the etching system 50 (e.g., via a chemical recirculation flow of a working fluid, such as phosphoric acid) or via a remote sample pump 121 coupled to the valve 110 to pull the sample 112 from the etching system 50 into the remote sampling system 104. In implementations, prior to entry into the valve 110, the sample 112 is cooled (e.g., via a concentric circulation system, a thermo-electric device, or the like) to control the sample temperature. For example, with hot phosphoric acid, the temperature of the phosphoric acid may be cooled to a temperature from about 30° C. to about 100° C. before being introduced to the valve 110. Such temperatures can avoid damaging the valve system (e.g., a fluoropolymer valve system) while preventing formation of sample gels or having highly viscous concentrated phosphoric acid interfering with the sampling process.

When the sample 112 is collected from the etching system 50 (e.g., via syringe pump 120, remote sample pump 121, etching system 50 pressure, etc.), the sample 112 can be directed into the valve 110 with the valve 110 in a sampling configuration, where the sample 112 is directed into a holding loop 122. The valve 110 can then switch configurations to a transfer configuration, where the carrier pump 114, the diluent pump 116, and the standard pump 118 operate to provide one or more of carrier, diluent, and standard to the valve 110. The system 100 provides inline dilution of the sample 112 when the diluent pump 116 operates to supply diluent fluid to the valve 110 via diluent line 117, whereby the diluent fluid can mix with the sample inline (e.g., via the mixing port of the valve 110, downstream of the valve 110, or the like). Similarly, the introduction of standard to the sample occurs via inline introduction of the standard to the sample at the valve 110 via operation of the standard pump 118. In an implementation, the amount of carrier, diluent, and standard provided to the valve 110 is determined analytically (e.g., via a controller in the analysis system 102), such as to provide automatic calibration or inline dilution of the sample 112, which can be based on a user-input, a quality control parameter based on the etching system 50, or a combination thereof. For example, in implementations the system 100 automatically calibrates the analysis system 102 in the sample matrix (e.g., phosphoric acid matrix, method of standard addition (MSA) spike, etc.) or adds internal standard for accurate measurements.

The sample 112 is then transferred from the holding loop 122 into a transfer line 124 (which in implementations involves dilution or standard addition via a mixing port of the valve 110 coupled with the transfer line 124), where the transfer line 124 is coupled between the valve 110 of the remote sampling system 104 and the analysis system 102. For example, in an implementation the transfer line 124 is coupled between the valve 110 of the remote sampling system 104 and a local sample valve 126 of the analysis system 102 (e.g., in a sample receive configuration), where excess fluid can be purged to waste 136. The local sample valve 126 can be a multi-position valve in fluid communication with one or more additional pumps 134 (e.g., syringe set(s)) of the analysis system 102 for transfer of fluids between the valve 110 and the local sample valve 126 (e.g., through the transfer line 124), from the local sample valve 126 to the analysis device 128, for rinse or cleaning procedures, and so forth. The local sample valve 126 can switch from the sample receive configuration to a sample deliver configuration where the sample is delivered to the analysis device 128. For example, when in the sample deliver configuration, the carrier (supplied via one or more of the carrier pump 114 or pump 134) delivers the diluted sample (which can also include a standard spike) to a nebulizer of an ICP analyzer of the analysis device 128. In an implementation, the standard pump 120 pushes the diluted sample from the valve 110 through the transfer line 124 to the local sample valve 126. In implementations, the sample delivery to the analysis device 128 is preceded by a rinse procedure of the analysis device 128.

Thermally-Controlled Transfer

Figure 3A:
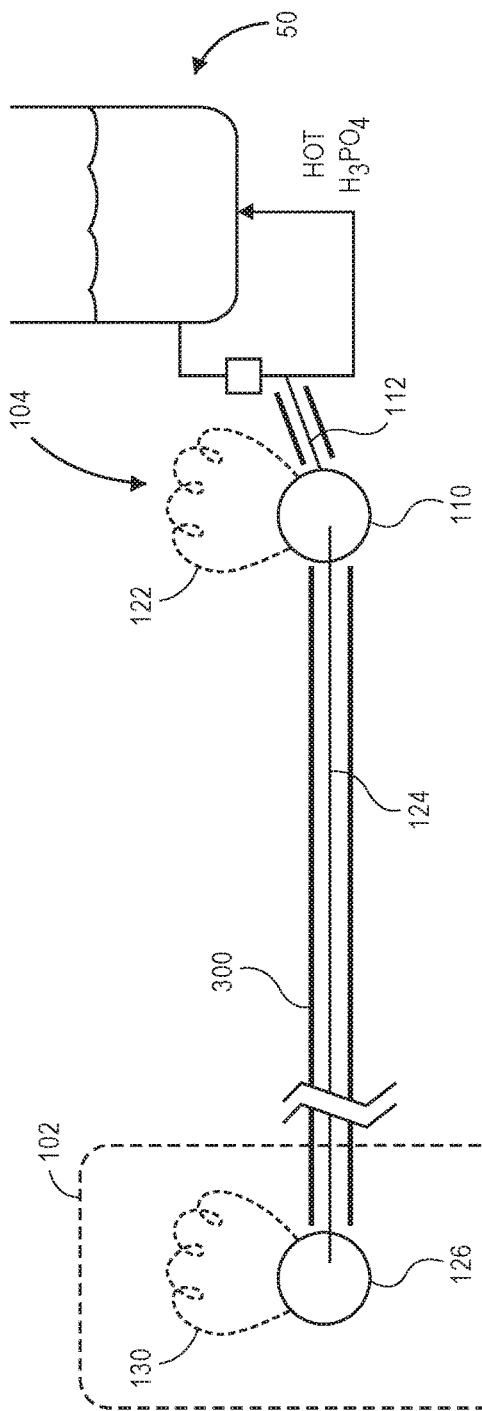
FIG. 3A is a schematic illustration of a controlled sample transfer line having a thermal sheath in accordance with example implementations of the present disclosure.
Figure 3B:
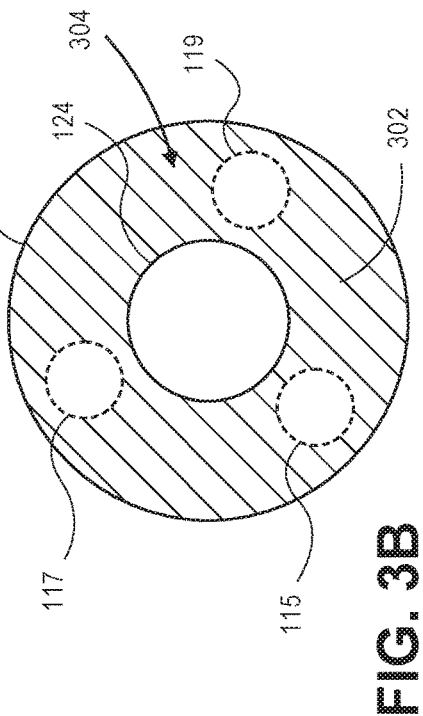
FIG. 3B is a cross-sectional view of the controlled sample transfer line having a thermal sheath of FIG. 3A in accordance with example implementations of the present disclosure.

Referring to FIGS. 3A and 3B, the system 100 includes a thermal sheath 300 to facilitate a temperature controlled transfer line 124 between the remote sampling system 104 and the analysis system 102 in accordance with example implementations of the present disclosure. The temperature of the sample can be controlled to facilitate or enable transfer between the remote sampling system 104 and the analysis system 102. For example, with hot phosphoric acid, the thermal sheath 300 can cool or maintain the phosphoric acid at a temperature from about 30° C. to about 100° C. during delivery through the transfer line 124. Such temperatures can avoid damaging valves of the system 100 while preventing formation of sample gels and/or preventing highly viscous concentrated phosphoric acid interfering with the transfer process through the transfer line 124. Further, by controlling the viscosity of the sample within the transfer line 124, the system 100 can avoid introducing impurities to the sample 112 via extraction of impurities from the valve 110, such as when the sample fluid is too viscous.

In an implementation, the thermal sheath 300 facilitates temperature control via a recirculating fluid in contact with the transfer line 124, but not in contact with the sample 112 therein. For example, as shown in FIG. 3B, the thermal sheath 300 and the transfer line 124 can form concentric tubes with the transfer line 124 in an interior region and with the thermal sheath 300 surrounding the transfer line 124. A fluid 302 (e.g., a temperature-regulated recirculating fluid) can flow through an annular region 304 surrounding the transfer line 124 to facilitate temperature control of the sample 112 within the transfer line 124. In an implementation, the fluid 302 within the thermal sheath 300 is water at a temperature of from about 50° C. to about 100° C., which can be recirculated and controlled to maintain an accurate temperature to thermally regulate the temperature of the sample 112 within the transfer line 124. In an implementation, one or more of the carrier line 115, the diluent line 117, or the standard line 119 is located in the annular region 304 of the thermal sheath 300. Such a configuration can facilitate temperature control of the carrier, diluent, and standard prior to introducing the carrier, diluent, and standard to the sample 112 at the remote valve 110, which can provide precise dilution factors, mixing conditions, or the like. In an implementation, one or more of the carrier line 115, the diluent line 117, or the standard line 119 is supported by a separate sheath (which can optionally be thermally-regulated) than the thermal sheath.

In an implementation, the thermal sheath 300 facilitates temperature control via a thermally conductive medium in thermal contact with the transfer line 124. For example, the thermal sheath 300 can include a thermally conductive material (e.g., a ceramic material, a metallic material, a combination of a ceramic and a metal, etc.) in contact with or in close proximity to the transfer line 124 to thermally regulate the temperature of the sample 112 flowing within the transfer line 124. The temperature of the thermal sheath 300 is controlled to thereby control the temperature of the sample 112 flowing within the transfer line 124. For example, the thermal sheath 300 can be in contact with a recirculating fluid to thermally regulate the thermal sheath 300, the thermal sheath 300 can be coupled with a thermal electric device to thermally regulate the thermal sheath 300, or a combination thereof.

In implementations, the analysis system 102 includes a local sample loop 130 coupled to the local sample valve 126 for holding the sample 112 received from the thermally regulated transfer line 124, such as to facilitate automatic dilution or calibration of the sample 112 at the analysis system 102 prior to analysis by the analysis device 128. Further, in implementations, the analysis system 102 may include a sampling device 132 configured to collect a sample 112 that is local to the analysis system 102.

Figure 4:
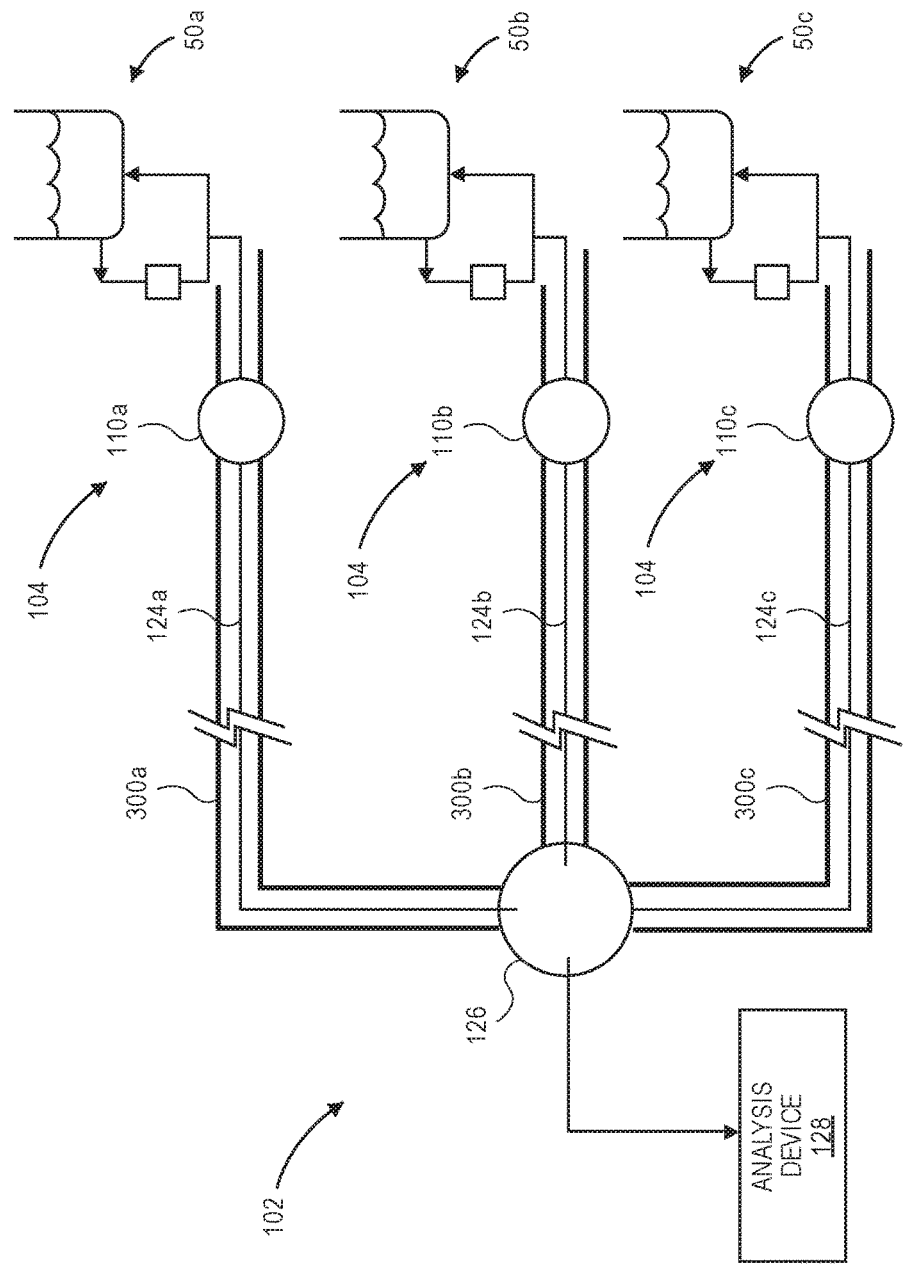
FIG. 4 is a schematic illustration of a plurality of controlled sample transfer lines each having a thermal sheath in accordance with example implementations of the present disclosure.

In implementations, the analysis system 102 is coupled to a plurality of remote sampling systems 104. For example the local sample valve 126 can be configured as a multi-position valve in fluid communication with a plurality of remote sampling valves 110 via a plurality of thermally regulated transfer lines 124 (e.g., the transfer line 124 is thermally-regulated via thermal sheath 300). For example, as shown in FIG. 4, the local sample valve 126 is positioned at a first location (e.g., proximate to the analysis system 102) and is coupled with a first remote sample valve 110*a* at a second location via a first thermally-regulated transfer line 124*a* with thermal sheath 300*a*, is coupled with a second remote sample valve 110*b* at a third location via a second thermally-regulated transfer line 124*b* with thermal sheath 300*b*, and is coupled with a third remote sample valve 110*c* at a fourth location via a third thermally-regulated transfer line 124*c* with thermal sheath 300*c*. Each of the plurality of remote sampling valves (e.g., 110*a*, 110*b*, and 110*c*) are configured to receive a sample from respective etching systems (50*a*, 50*b*, and 50*c*) to provide a plurality of samples for analysis by the analysis system 102. While three sample systems are shown, it is contemplated that fewer sample systems or more sample systems can be present for analysis by the system 100. As such, the system 100 can be configured to hold multiple prepped samples for analysis to provide a high throughput system capable of multiple samples collected from multiple remote locations.

Control of Silicon Fabrication Process Conditions

Figure 5:
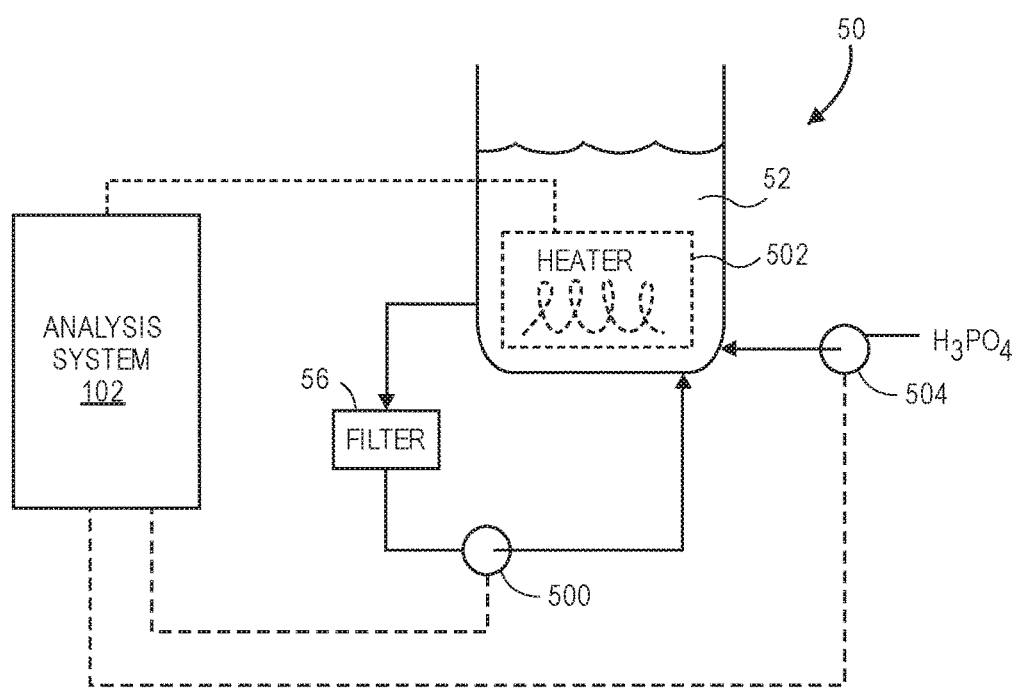
FIG. 5 is a schematic illustration of a control protocol of an etching system via one or more outputs of a remote analysis system for automatic analysis of chemical element concentrations in accordance with example implementations of the present disclosure.

In implementations, analysis of the sample 112 by the analysis system 102 can result in data for automatic control of one or more process devices of the etching system 50. Referring to FIG. 5, the analysis system 102 is communicatively coupled to the etching system 50, whereby the data provided by the analysis system 102 can facilitate automatic control of one or more process devices of the etching system 50. For example, the analysis system 102 can report concentration data of one or more elements (e.g., silicon, tungsten, copper, titanium, etc.), organic species, inorganic species, or the like via one or more communications protocols to provide a control signal to automatically manipulate a control device of the etching system 50, including but not limited to, a recirculation pump 500 (or controller thereof) to control a rate of recirculation of the working fluid (e.g., phosphoric acid) in the recirculation line 54, a heater 502 (or controller thereof) to control a temperature of the bath 52, a pump 504 (or controller thereof) to control the rate at which fresh phosphoric acid is provided to the acid bath 52, or so forth. For instance, in an implementation, feedback is provided from the system 100 to a wetbench system (e.g., etching system 50) to automatically control the addition of fresh phosphoric acid to dilute silicon concentrations within the acid bath 52 to desired concentration levels (e.g., within about 50 ppm Si). Further, the system 100 can utilize the concentration data to control a speed of production of the etching system 50, since the production rate of the semiconductor product can be correlated with silicon concentration to determine a peak production rate based on silicon concentration of the acid bath 52.

For example, the system 100 can include a computing device including a processor and a memory. The processor provides processing functionality for the computing device and may include any number of processors, micro-controllers, or other processing systems, and resident or external memory for storing data and other information accessed or generated by the computing device. The processor may execute one or more software programs that implement the techniques and modules described herein. The processor is not limited by the materials from which it is formed or the processing mechanisms employed therein and, as such, may be implemented via semiconductor(s) and/or transistors (e.g., electronic integrated circuits (ICs)), and so forth.

The memory is an example of device-readable storage media that provides storage functionality to store various data associated with the operation of the computing device, such as the software program and code segments mentioned above, or other data to instruct the processor and other elements of the computing device to perform the techniques described herein. Although a single memory is mentioned above, a wide variety of types and combinations of memory may be employed. The memory may be integral with the processor, stand-alone memory, or a combination of both. The memory may include, for example, removable and non-removable memory elements such as RAM, ROM, Flash (e.g., SD Card, mini-SD card, micro-SD Card), magnetic, optical, USB memory devices, and so forth. In embodiments of the computing device, the memory may include removable ICC (Integrated Circuit Card) memory such as provided by SIM (Subscriber Identity Module) cards, USIM (Universal Subscriber Identity Module) cards, UICC (Universal Integrated Circuit Cards), and so on.

The computing device includes a display to display information to a user of the computing device. In embodiments, the display may comprise a CRT (Cathode Ray Tube) display, an LED (Light Emitting Diode) display, an OLED (Organic LED) display, an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display may be backlit via a backlight such that it may be viewed in the dark or other low-light environments.

The display may be provided with a touch screen to receive input (e.g., data, commands, etc.) from a user. For example, a user may operate the computing device by touching the touch screen and/or by performing gestures on the touch screen. In some embodiments, the touch screen may be a capacitive touch screen, a resistive touch screen, an infrared touch screen, combinations thereof, and the like. The computing device may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

The computing device may also include a communication module representative of communication functionality to permit computing device to send/receive data between different devices (e.g., components/peripherals) and/or over one or more networks. Communication module may be representative of a variety of communication components and functionality including, but not necessarily limited to: a browser; a transmitter and/or receiver; data ports; software interfaces and drivers; networking interfaces; data processing components; and so forth.

The one or more networks are representative of a variety of different communication pathways and network connections which may be employed, individually or in combinations, to communicate among the components of the system 100 and/or of the etching system 50. Thus, the one or more networks may be representative of communication pathways achieved using a single network or multiple networks. Further, the one or more networks are representative of a variety of different types of networks and connections that are contemplated including, but not necessarily limited to: the Internet; an intranet; a Personal Area Network (PAN); a Local Area Network (LAN) (e.g., Ethernet); a Wide Area Network (WAN); a satellite network; a cellular network; a mobile data network; wired and/or wireless connections; and so forth.

Examples of wireless networks include, but are not necessarily limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through Universal Serial Bus (USB), Ethernet, serial connections, and so forth.

The computing device is described as including a user interface, which is storable in memory and executable by the processor. The user interface is representative of functionality to control the display of information and data to the user of the computing device via the display. In some implementations, the display may not be integrated into the computing device and may instead be connected externally using universal serial bus (USB), Ethernet, serial connections, and so forth. The user interface may provide functionality to allow the user to interact with one or more applications of the computing device by providing inputs (e.g., sample identities, desired dilution factors, spiking protocols, etc.) via the touch screen and/or the I/O devices. For example, the user interface may cause an application programming interface (API) to be generated to expose functionality to a dilution or temperature control module to configure the application for display by the display or in combination with another display. In embodiments, the API may further expose functionality to configure an inline dilution control module, an etching process control module, or a combination thereof, to allow the user to interact with an application by providing inputs via the touch screen and/or the I/O devices to provide desired dilution factors for analysis.

The inline dilution control module and/or the etching process control module may comprise software, which is storable in memory and executable by the processor, to perform a specific operation or group of operations to furnish functionality to the computing device. The inline dilution control module provides functionality to control the dilution of, for example, an internal standard and/or the samples from the remote sampling system 104. For example, the inline dilution control module may control amounts of the carrier and/or the diluent that are supplied by one or more pumps of the system. The etching process control module provides functionality to control one or more process conditions or devices of the etching system 50, such as to control the concentration of one or more chemical elements present in a working fluid of the etching system. For example, the etching process control module may control the pump rate of hot phosphoric acid to the acid bath 52, control a temperature of the acid bath 52, a pump rate of fresh phosphoric acid provided to the acid bath 52, or so forth, or provide a controlled concentration of a chemical element (e.g., silicon) therein.

In implementations, the user interface may include a browser (e.g., for implementing functionality of the control modules described herein). The browser enables the computing device to display and interact with content such as a webpage within the World Wide Web, a webpage provided by a web server in a private network, and so forth. The browser may be configured in a variety of ways. For example, the browser may be configured as an inline dilution control module or etching process control module accessed by the user interface. The browser may be a web browser suitable for use by a full resource device with substantial memory and processor resources (e.g., a smart phone, a personal digital assistant (PDA), etc.).

Generally, any of the functions described herein can be implemented using software, firmware, hardware (e.g., fixed logic circuitry), manual processing, or a combination of these implementations. The terms "module" and "functionality" as used herein generally represent software, firmware, hardware, or a combination thereof. The communication between modules in the system 100, for example, can be wired, wireless, or some combination thereof. In the case of a software implementation, for instance, a module may represent executable instructions that perform specified tasks when executed on a processor, such as the processor described herein. The program code can be stored in one or more device-readable storage media, an example of which is the memory associated with the computing device.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A system comprising:
a remote sampling system configured to collect a sample of phosphoric acid at a first location, the sample of phosphoric acid collected at the first location being at least about 150 degree, the remote sampling system including a remote valve having a holding loop coupled thereto through which the sample of phosphoric acid is configured to selectably flow; and an analysis system configured for positioning at a second location remote from the first location, the analysis system coupled to the remote valve via a transfer line, the analysis system including an analysis device configured to determine a concentration of one or more components of the sample of phosphoric acid and including a sample pump at the second location configured to introduce the sample from the holding loop into the transfer line for analysis by the analysis device.

2. The system of claim 1, wherein the sample of phosphoric acid has a temperature from about 150° C. to about 180° C. at the first location.

3. The system of claim 1, wherein the analysis system further includes a local sample valve coupled to the remote valve via the transfer line and coupled to the analysis device.

4. The system of claim 1, further comprising:
a thermal sheath surrounding at least a portion of the transfer line.

5. The system of claim 4, wherein the thermal sheath includes a temperature-regulated fluid in an annular region between the thermal sheath and the transfer line.

6. The system of claim 1, wherein the analysis system includes at least one of a carrier pump coupled to the remote valve via a carrier fluid line, a diluent pump coupled to the remote valve via a diluent fluid line, or a standard pump coupled to the remote valve via a standard fluid line.

7. The system of claim 6, further comprising:
a thermal sheath surrounding at least a portion of the transfer line and at least one of the carrier fluid line, the diluent fluid line, or the standard fluid line.

8. The system of claim 7, wherein the thermal sheath includes a temperature-regulated fluid in an annular region between the thermal sheath and the transfer line.

9. The system of claim 7, wherein the at least one of the carrier fluid line, the diluent fluid line, or the standard fluid line is positioned in an annular region between the thermal sheath and the transfer line.

10. The system of claim 1, further including a communicative coupling, the communicative coupling configured to provide a control signal between the analysis system and one or more of a heater of a phosphoric acid etching system at the first location, a recirculation pump configured to recirculate phosphoric acid of the phosphoric acid etching system, or a pump configured to introduce fresh phosphoric acid to the phosphoric acid etching system.

11. The system of claim 10, wherein the control signal is based on the concentration of one or more components of the sample of phosphoric acid determined by the analysis system.

12. The system of claim 10, wherein the control signal is configured to maintain a silicon concentration in the phosphoric acid etching system within about 50 ppm.

13. A method, comprising:
receiving a sample of phosphoric acid at a first location with a remote sampling system, the phosphoric acid received at the first location being at least about 150 degree;
introducing the sample of phosphoric acid into a holding loop of the remote sampling system via operation of a pump positioned at a second location remote from the first location or a local sample pump positioned at the first location;
introducing at least one of a carrier fluid, a diluent fluid, or a standard fluid to the sample of phosphoric acid at the remote sampling system;
transferring the sample of phosphoric acid from the remote sampling system through a transfer line to the second location via operation of a second pump positioned at the second location; and
determining a concentration of a chemical element in the sample of phosphoric acid via an analysis device at the second location.

14. The method of claim 13, wherein the sample of phosphoric acid has a temperature from about 150° C. to about 180° C. at the first location.

15. The method of claim 13, further comprising:
controlling a temperature of the sample of phosphoric acid during the step of transferring the sample of phosphoric acid from the remote sampling system through the transfer line to the second location via operation of the second pump positioned at the second location.

16. The method of claim 15, wherein controlling a temperature of the sample of phosphoric acid includes transferring the sample of phosphoric acid from the remote sampling system through the transfer line, wherein the transfer line is positioned concentrically within a thermal sheath.

17. The method of claim 16, wherein at least one of a carrier fluid line, a diluent fluid line, or a standard fluid line is positioned in a region between the transfer line and the thermal sheath.

18. The method of claim 15, wherein controlling the temperature of the sample of phosphoric acid during the step of transferring the sample of phosphoric acid includes at least one of cooling the sample of phosphoric acid to, or maintaining the sample of phosphoric acid at, a temperature from about 30° C. to about 100° C.

19. The method of claim 13, further comprising:
providing a control signal to one or more of a heater of a phosphoric acid etching system at the first location, a recirculation pump configured to recirculate phosphoric acid of the phosphoric acid etching system, or a pump configured to introduce fresh phosphoric acid to the phosphoric acid etching system, the control signal based on the concentration of the chemical element in the sample of phosphoric acid determined via the analysis device at the second location.

20. The method of claim 19, wherein the control signal is configured to maintain a silicon concentration in the phosphoric acid etching system within about 50 ppm.

* * * * *